(12) United States Patent
Zhang et al.

(10) Patent No.: US 9,441,116 B2
(45) Date of Patent: Sep. 13, 2016

(54) AQUEOUS POLYMER DISPERSION

(75) Inventors: Tingke Zhang, Shanghai (CN);
Qingwei Zhang, Shanghai (CN)

(73) Assignee: Rohm and Haas Company, Philadelphia, PA (US)

( * ) Notice: Subject to any disclaimer, the term of this patent is extended or adjusted under 35 U.S.C. 154(b) by 49 days.

(21) Appl. No.: 14/346,844

(22) PCT Filed: Oct. 11, 2011

(86) PCT No.: PCT/CN2011/080632
§ 371 (c)(1),
(2), (4) Date: Mar. 24, 2014

(87) PCT Pub. No.: WO2013/053101
PCT Pub. Date: Apr. 18, 2013

(65) Prior Publication Data
US 2014/0213692 A1    Jul. 31, 2014

(51) Int. Cl.
| | |
|---|---|
| *A61K 8/81* | (2006.01) |
| *C09D 5/14* | (2006.01) |
| *A61K 8/44* | (2006.01) |
| *A61K 9/10* | (2006.01) |
| *C09D 133/14* | (2006.01) |
| *C08K 5/17* | (2006.01) |
| *C08K 5/00* | (2006.01) |

(52) U.S. Cl.
CPC . *C09D 5/14* (2013.01); *A61K 8/44* (2013.01); *A61K 9/10* (2013.01); *C08K 5/175* (2013.01); *C09D 133/14* (2013.01); *C08K 5/0091* (2013.01)

(58) Field of Classification Search
CPC ...... C09D 5/14; C09D 133/14; C08K 5/175; C08K 5/0091; A61K 8/44; A61K 9/10
See application file for complete search history.

(56) References Cited

U.S. PATENT DOCUMENTS

| | | |
|---|---|---|
| 5,264,530 A | 11/1993 | Darmon et al. |
| 5,356,968 A | 10/1994 | Rupaner et al. |
| 5,494,961 A | 2/1996 | Lavoie et al. |
| 5,525,662 A | 6/1996 | Lavoie et al. |
| 5,698,108 A | 12/1997 | Okun |
| 7,390,774 B2 | 6/2008 | Ghosh et al. |
| 8,877,256 B2 | 11/2014 | Dudnik et al. |
| 2011/0160368 A1 | 6/2011 | Bohling et al. |

FOREIGN PATENT DOCUMENTS

| | | |
|---|---|---|
| CN | 102115513 A | 7/2011 |
| EP | 2341094 A2 | 7/2011 |
| JP | 2011152439 A | 8/2011 |
| WO | 2009015476 A1 | 2/2009 |
| WO | 2009143110 A1 | 11/2009 |

*Primary Examiner* — Gregory Listvoyb
(74) *Attorney, Agent, or Firm* — Karl E. Stauss; Cantor Colburn LLP

(57) ABSTRACT

The present invention relates generally to an aqueous polymer dispersion and a coating composition made thereof, especially to a "green" antibacterial polymer dispersion with improved color stability property upon exposure to heat and/or light, and the coating composition made thereof.

9 Claims, No Drawings

AQUEOUS POLYMER DISPERSION

BACKGROUND

The present invention relates generally to an aqueous polymer dispersion and a coating composition made thereof, especially to a "green" antibacterial polymer dispersion with improved color stability property upon exposure to heat and/or light, and the coating composition made thereof.

Inorganic microbiocides on which metal ions are supported frequently exhibit instabilities which cause them to discolor upon exposure to heat or sun light. Hence, these inorganic microbiocides frequently cause aqueous binder emulsion and coating compositions into which they are incorporated to undergo conspicuous changes in coloration. Accordingly, the use of these microbiocides is effectively limited to systems for which such conspicuous changes in coloration can be tolerated.

U.S. Pat. No. 7,390,774 discloses a light stable antimicrobial composition comprising a metal complexed with a polymer containing 1-vinylimidazole as monomer, wherein the metal is selected from copper, silver, gold, tin, zinc and combinations thereof. The antimicrobial composition exhibits better light stable property than the conventional inorganic microbiocides consisting of metal ions supported by materials including active carbon, apatite, zeolite, and various phosphates. However, a higher level of color stability is still desired. Moreover, the antimicrobial composition comprising a metal complexed with a polymer needs some kind of organic solvent and ammonia to help incorporation, which increases the total volatile organic compound (VOC) content of the coating composition and causes bad odor. Low VOC and ammonia free are also desired.

The problem addressed by the present invention is to find an improved aqueous antibacterial polymer dispersion which shows lower discoloration of the corresponding formulations upon exposure to heat and/or sun light as compared to the antimicrobial composition of the U.S. Pat. No. 7,390,774. Moreover, the present invention also provides an antibacterial polymer dispersion comprising a metal complex with a polymer that is stripped by steam to reduce the VOC for low VOC and low odor request.

STATEMENT OF INVENTION

The present invention provides an aqueous polymer dispersion comprising: a) a polymer comprising, as polymerized units, from 0.1% to 10% by dry weight percentage based on the dry weight of the polymer dispersion, at least one acetoacetoxy or acetoacetamide group containing monomer; b) 0.001% to 0.15% by dry weight percentage based on the dry weight of the polymer dispersion, at least one metal ion; and c) an amino acid, being present in the mole ratio of amino acid/acetoacetate or acetoacetamide group containing monomer from 0.9:1 to 5:1.

The present invention further provides a coating composition comprising the aqueous polymer dispersion as mentioned above.

DETAILED DESCRIPTION

For the purpose of describing the components in the compositions of the present invention, all phrases comprising parenthesis denote either or both of the included parenthetical matter and its absence. For example, the phrase "(co)polymer" includes, in the alternative, polymer, copolymer and mixtures thereof; the phrase "(meth)acrylate" means acrylate, methacrylate, and mixtures thereof, and the phrase "(meth)acrylic" used herein means acrylic, methacrylic, and mixtures thereof.

As used herein, the term "aqueous polymer dispersion" refers to a composition containing discrete polymer particles dispersed in an aqueous medium, for example, aqueous polymer emulsion.

As used herein, the term "pendant" means "attached to the polymer backbone as a side group, but not within the polymer backbone". The term "pendant" also includes attachment of such a group at the termini of a polymer chain.

As used herein, the term "up to" in a range means any and all amounts greater than zero and through to and including the end point of the range. As used herein, unless otherwise indicated, the unit "wt %" shall mean a dry weight percentage based on total dry weight of polymerized monomers. "Glass transition temperature" or "Tg" used herein are those calculated by using the Fox equation (T. G. Fox, Bull. Am. Physics Soc., Volume 1, Issue No. 3, page 123(1956)). That is, for calculating the Tg of a copolymer of monomers $M_1$ and $M_2$, $$\frac{1}{T_g(calc.)} = \frac{w(M_1)}{T_g(M_1)} + \frac{w(M_2)}{T_g(M_2)}$$

wherein Tg (calc.) is the glass transition temperature calculated for the copolymer, $w(M_1)$ is the weight fraction of monomer $M_1$ in the copolymer, $w(M_2)$ is the weight fraction of monomer $M_2$ in the copolymer, $T_g(M_1)$ is the glass transition temperature of the homopolymer of $M_1$, and $T_g(M_2)$ is the glass transition temperature of the homopolymer of $M_2$, all temperatures being in K. The glass transition temperatures of homopolymers may be found, for example, in "Polymer Handbook", edited by J. Brandrup and E. H. Immergut, Interscience Publishers.

The aqueous polymer dispersion of the present invention comprises (co)polymer(s) comprising, as (co)polymerized units, a monomer having at least one acetoacetoxy or acetoacetamide functional group. The level of the monomer ranges from 0.1% to 10%, preferably from 0.1% to 8%, more preferably 0.1 to 5%, by dry weight percentage based on the total dry weight of the polymer dispersion.

The acetoacetoxy or acetoacetamide groups are represented by:

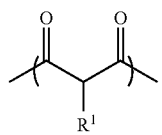

wherein $R^1$ is hydrogen, or alkyl having 1 to 10 carbon atoms, or phenyl.

Examples of acetoacetoxy or acetoacetamide functional groups are:

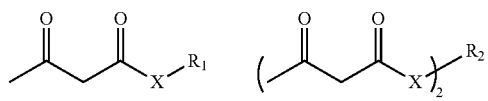

Wherein X is O or N, $R_1$ is a divalent radical and $R_2$ is a trivalent radical, that attach the acetoacetoxy or acetoacetamide functional group to the polymer backbone or as dispersed in aqueous medium. Suitable levels of acetoacetoxy or acetoacetamide functional groups may be in the range of from $1\times10^{-6}$ to $8\times10^{-4}$ mole of acetoacetoxy or acetoacetamide functional groups per gram of acetoacetoxy or acetoacetamide functional polymer particles.

The acetoacetoxy or acetoacetamide functional polymer particles can be prepared by polymerization of acetoacetoxy or acetoacetamide functional monomer, nonionic monomer, and optionally, ionic monomer.

Acetoacetoxy or acetoacetamide functional monomers are monomers having an ethylenic unsaturation and one or more acetoacetyl moieties. These acetoacetyl functional monomers have the following structures:

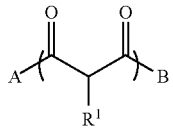

wherein A is either:

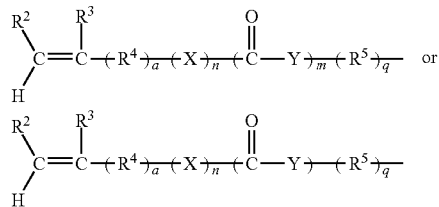

wherein $R^1$ is selected from H, alkyl having 1 to 10 carbon atoms, and phenyl; $R^2$ is selected from H, alkyl having 1 to 10 carbon atoms, phenyl, halo, $CO_2CH_3$, and CN; wherein $R^3$ is selected from H, alkyl having 1 to 10 carbon atoms, phenyl, and halo; wherein $R^4$ is selected from alkylene having 1 to 10 carbon atoms and phenylene; wherein $R^5$ is selected from alkylene having 1 to 10 carbon atoms and phenylene; wherein a, m, n, and q are independently selected from 0 and 1; wherein each of X and Y is selected from —NH— and —O—; and B is selected from A, alkyl having 1 to 10 carbon atoms, phenyl, and heterocyclic groups. Examples of the acetoacetoxy functional monomers include, among the following, acetoacetoxyalkyl (meth)acrylates such as acetoacetoxyethyl (meth)acrylate, acetoacetoxypropyl (meth)acrylate, acetoacetoxybutyl (meth)acrylate, and 2,3-di(acetoacetoxy) propyl (meth)acrylate; allyl acetoacetate; vinyl acetoacetate; various acetoacetamides, including, but not limited to:

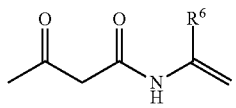

wherein $R^6$ is either H or methyl; and combinations thereof.

Preferred acetoacetoxy functional monomers include acetoacetoxyethyl(meth)acrylate, acetoacetoxypropyl(meth)acrylate, acetoacetoxybutyl (meth)acrylate, allyl acetoacetate, 2,3-di(acetoacetoxy)propyl(meth)acrylate, and combinations thereof.

In one embodiment of the present invention, the acetoacetoxy or acetoacetamide functional (co)polymer(s) comprises nonionic polymerized monomers. A "nonionic monomer" herein is a monomer that contains at least one ethylenic unsaturated but does not have a pendant acid or base group. Examples of the nonionic monomers include: butadiene; vinyl naphthalene; ethylene; propylene; vinyl acetate; vinyl versatate; vinyl chloride; vinylidene chloride; acrylonitrile; various $C_1$-C40 alkyl esters of (meth)acrylic acid, such as methyl (meth)acrylate, ethyl (meth) acrylate, n-butyl (meth)acrylate, 2-ethylhexyl (meth) acrylate, cyclohexyl (meth)acrylate, n-octyl (meth) acrylate, n-decyl (meth) acrylate, n-dodecyl (meth)acrylate, tetradecyl (meth)acrylate, lauryl (meth)acrylate, oleyl (meth)acrylate, palmityl (meth)acrylate, and stearyl (meth)acrylate; other (meth)acrylates such as isobornyl (meth)acrylate, benzyl (meth) acrylate, phenyl (meth)acrylate, and 2-bromoethyl (meth)acrylate; alkoxyalkyl (meth) acrylates, such as ethoxyethyl (meth)acrylate; full esters of ethylenically unsaturated di- and tricarboxylic acids and anhydrides, such as diethyl maleate, dimethyl fumarate, ethyl methyl itaconate; and styrene and substituted styrenes, such as 4-methylstyrene, and 2-methylstyene. Other suitable nonionic monomers include multiethylenically unsaturated monomers, which are effective for increasing the molecular weight of the polymer particles. Examples of the multiethylenically unsaturated monomers include tripropylene glycol di(meth)acrylate, diethylene glycol di(meth)acrylate, ethylene glycol di(meth)acrylate, 1,6-hexanediol di(meth)acrylate, 1,3-butylene glycol di(meth)acrylate, polyalkylene glycol di(meth)acrylate, diallyl phthalate, trimethylolpropane tri(meth)acrylate, allyl (meth)acrylate, divinylbenzene, divinyltoluene, trivinylbenzene, and divinyl naphthalene. Suitable levels of (co)polymerized nonionic monomer in the polymer ranges from 50 to 99.9 wt %, preferably from 60 to 95 wt %, and more preferably from 700 to 95 wt %, based on the total weight of the polymer dispersion.

The acetoacetoxy or acetoacetamide functional (co)polymer optionally includes, as polymerized units, at least one additional ionic monomer. The (co)polymerized ionic monomer may be included in the acetoacetoxy or acetoacetamide functional polymer particles to help stabilize the polymer particles in the aqueous medium. The ionic monomer may be an anionic monomer or alternatively, a cationic monomer. As used herein, "anionic monomer" refers to an ionic monomer that contains at least one pendant acid group or salt thereof. Examples of the anionic monomer include carboxylic acid containing monomers such as (meth)acrylic acid, itaconic acid, fumaric acid, and maleic acid; anhydrides, which can form carboxylic acid monomers in the presence of water, such as itaconic anhydride and maleic anhydride; and partial esters of multicarboxylic acid monomers, such as ethyl maleate. Other examples of acid containing monomers are phosphorus acid monomers such as 2-phosphoethyl (meth)acrylate; and sulfur acid monomers such as sodium vinyl sulphonate, 2-acrylamido-2-methylpropane sulfonic acid, vinyl sulphonic acid, sulfoethyl (meth)acrylate, and methacryloxyisopropyl acid sulfophthalate, and hydroxy, dihydroxy, amino or diamino alkyl or aryl sulfonic acids, such as, 1,4-butanediol 2-sulfonic acid. As used herein, "cationic monomer" refers to an ionic monomer that contains at least one pendant base group or salt thereof. The cationic monomer expressly excludes acetoacetoxy or acetoacetamide functional monomer (b). Examples of the cationic monomer include amine functional monomers such as, for example, 2-vinoxyethylamine, 2-vinoxyethylethylene-diamine, 3-aminopropyl vinyl ether, 2-amino-2-methylpropyl vinyl ether, and 2-aminobutyl vinyl ether; and amide containing monomers such as (meth) acrylamide, dimethylaminoethyl (meth)acrylate, and oxazolidinoethyl (meth) acrylate. In certain non-limiting embodiments, the acetoacetoxy or acetoacetamide functional polymer particle contains as polymerized units both anionic monomer and cationic monomer. Suitable levels of the polymerized ionic monomer in the acetoacetoxy or acetoacetamide functional polymer range up to 40 wt %, preferably from 0.1 to 10 wt %, and more preferably, from 0.1 to 5 wt %, based on the total weight of the polymer dispersion. The acetoacetoxy or acetoacetamide functional polymer may contain one or more polymerized ionic monomers.

The types and levels of the acetoacetoxy or acetoacetamide functional monomer, the nonionic monomer, and the optional ionic monomer may be chosen to provide the acetoacetoxy or acetoacetamide functional (co)polymer with a glass transition temperature suitable for an intended end use. Suitable ranges for the glass transition temperature of the acetoacetoxy or acetoacetamide functional (co)polymer include the range of from −60° C. to 100° C., preferably the range of from −40° C. to 80° C. and more preferably the range of from −40° C. to 60° C.

Typically, the acetoacetoxy or acetoacetamide functional (co)polymer particles have an average diameter in the range of from 25 nanometers (nm) to 20 micron, preferably from 25 nm to 10 micron, and more preferably from 25 nm to 5 micron. The average polymer particle diameter may be determined by a quasi-elastic light scattering technique, using an instrument such as a BROOKHAVEN™ Model BI-90 Particle Sizer, supplied by Brookhaven Instruments Corporation, Holtsville, N. Y.

The acetoacetoxy or acetoacetamide functional (co)polymer of the present invention may be prepared by well known polymerization techniques, such as suspension polymerization or emulsion polymerization of ethylenically unsaturated monomers. Emulsion polymerization is preferred. Suitable processes are disclosed in U.S. Pat. No. 5,356,968 and U.S. Pat. No. 5,264,530. An alternate process to prepare the acetoacetoxy or acetoacetamide functional polymer particles is solution polymerization followed by the conversion of the solution polymer to the acetoacetoxy or acetoacetamide functional polymer particles by various methods known in the art. Suitable polymer processes, which include emulsion polymerization, solution polymerization, and suspension polymerization process, may be conducted as batch, semi-continuous, or continuous processes. Aqueous emulsion polymerization is a preferred process for preparing the acetoacetoxy functional polymer particles. Temperatures suitable for aqueous emulsion polymerization processes are in the range of from 20° C. to less than 100° C., preferably in the range of from 20° C. to 90° C. The polymerization processes commonly employ various synthesis adjuvants such as thermal or redox polymerization initiators, chain transfer agents, catalysts, surfactants, high molecular weight polymers, dispersants, salts, buffers, acids, or bases. Preferably the use of organic solvents is minimized in the polymerization process to provide an aqueous polymer dispersion with low levels of volatile organic compounds (VOCs). The aqueous polymer dispersion containing the acetoacetoxy or acetoacetamide functional polymer particles is optionally treated to remove VOCs by processes such as steam stripping or distillation.

The aqueous polymer dispersion of the present invention also contains an aqueous medium in which the acetoacetoxy or acetoacetamide functional polymer particles are dispersed. The aqueous medium optionally contains cosolvents including water miscible cosolvents such as methanol, ethanol, propanol, acetone, ethylene glycol ethyl ethers, propylene glycol propyl ethers, and diacetone alcohol; and water immiscible solvents such as propyl acetate, butyl acetate, methyl isoamyl ketone, amyl acetate, diisobutyl ketone, xylene, toluene, Coasol, Dalpad, butanol, and mineral spirits, preferably Coasol or Dalpad, as cosolvents. The aqueous polymer dispersion may be provided with 10 to 70 wt % polymer particles, based on the dry weight of the polymer dispersion. Preferably, one or more bases are added to the aqueous polymer dispersion to raise the pH to a value in the range of from 7 to 11, and more preferably in the range of from 7 to 9.5.

The aqueous polymer dispersion may contain acetoacetoxy or acetoacetamide functional polymer particles having a multimodal particle diameter distribution, such as a bimodal distribution. In one non-limiting embodiment, the aqueous polymer dispersion contains a small mode of acetoacetoxy or acetoacetamide functional polymer particles and a large mode of acetoacetoxy or acetoacetamide functional polymer particles, wherein the small mode has an average particle diameter in the range of from 25 to 150 nm, and the large mode has an average particle diameter of less than 1000 nm but larger than the average particle diameter of the small mode. Further, in this non-limiting embodiment, the ratio of the small mode acetoacetoxy or acetoacetamide functional polymer particles to the large mode acetoacetoxy or acetoacetamide functional polymer particles may be in the range of from 1:90 to 9:1 by weight.

The aqueous polymer dispersion of the present invention further comprises, by weight percentage based on the dry weight of the dispersion, from 0.001 to 0.15%, preferably from 0.003 to 0.1%, more preferably from 0.02 to 0.1%, at least one metal ion, wherein the metal is selected from copper, silver, gold, tin, and zinc, alternatively the metal is selected from copper, silver, and gold, alternatively the metal is selected from copper, and silver, alternatively the metal is silver.

The metal ion in the polymer dispersion of the present invention can be added in a form of metal ion solution, or a complex with polymer via coordination bond, ion bond or other weak interactions. It can be added in polymerization or post added to the aqueous polymer dispersion at room temperature or not higher than 80° C.

While not wanting to be bound as to the oxidation state of the silver ($Ag^0$, $Ag^{1+}$), that is incorporated into the aqueous dispersion or composition, silver may be added to the aqueous dispersion or composition by washing the polymer in a silver solution such as silver nitrate in deionized water ("DI"). Aside from DI, other liquid mediums can also be used such as water, aqueous buffered solutions and organic solutions such as polyethers or alcohols. Other sources of silver include but are not limited to silver acetate, silver citrate, silver iodide, silver lactate, silver picrate and silver sulfate. The concentration of silver in these solutions can vary from the concentration required to add a known quantity of silver to the aqueous dispersion or composition to a saturated silver solution.

In order to stabilize the silver ion in the acetoacetoxy or acetoacetamide functional aqueous dispersion of the present invention, at least an amino acid should be added to the aqueous dispersion. The suitable amino acid should be containing at least one mono-amine group and one carboxyl group, example of the suitable amino acid include gylcine, 3-aminopropanoic acid, 4-aminobutyric acid, 5-aminovaleric acid, 6-aminocaproric acid, 7-aminoheptanoic acid, serine, threonine, tyrosine and so on. The suitable level of amino acid in the aqueous polymer dispersion include the mole ratio of amino acid/acetoacetate or acetoacetamide group containing monomer from 0.9:1 to 5:1, preferably from 0.9:1 to 3:1, and more preferably from 0.9:1 to 2:1.

The aqueous acetoacetoxy or acetoacetamide functional polymer dispersion containing metal ion of the present invention is prepared by polymerizing of the nonanoic monomer with the acetoacetoxy or acetoacetamide functional monomer or mixing the nonanoinc (co)polymer with the non-polymeric acetoacetoxy or acetoacetamide functional compound; and essentially, mixed with the amino acid derivative having a mono-amine group, in or post the polymerization process. Above obtained acetoacetoxy or acetoacetamide functional polymer dispersion may be subjected to further deodorization processes including both or either of steam stripping and carboxylesterase enzyme treatment. The steam stripping can be proceeded for one to several cycles or passes to eliminate slight odor left in the dispersion. The carboxylesterase can be added to the aqueous dispersion at room temperature, then stay overnight or follow enzyme supplier's instruction to remove odorant substrate such as butyl acetate and butyl propionate from the dispersion, the metal ion can be added in polymerization process or post add as additives.

In addition, the aqueous polymer dispersion optionally includes other components, including other polymers, surfactants, pigments such as titanium dioxide, extenders, dyes, pearlescents, adhesion promoters, crosslinkers, dispersants, defoamers, leveling agents, optical brighteners, ultraviolet stabilizers, absorbing pigments, coalescents, rheology modifiers, preservatives, biocides, polymer particles having internal voids, and antioxidants. The aqueous polymer dispersion may contain coalescent in the amount of from 0 to 40 wt %, preferably 0 to 20 wt %, and more preferably 0 to 5 wt %, based on the dry weight of the (co)polymer. Preferably, the aqueous polymer dispersion is absent of coalescent.

The aqueous dispersion of the present invention is heat stable. The term "heat stable" of a polymer dispersion or a coating composition as used herein and in the appended claims refers to a durability characteristic of the polymer dispersion or the coating composition upon heating at a temperature of at least 40° C., alternatively at least 50° C., alternatively at least 80° C., alternatively at least 100° C. for a period of at least 10 days. The heat durability of the dispersion or the composition can be visual scored as from level 4 to level 0 which stands for from no visible change to heavy discoloration, as detailed described in the Example part. In the present invention, the discoloration upon such heating is acceptable when the visual scored level reaches level 3 or higher. By "acceptable" herein is meant sufficient coloration stability suitable for the application in the aqueous dispersion of the present invention. An embodiment with "acceptable" discoloration properties is regarded as within the scope of the present invention.

The present invention further provides an aqueous coating composition comprising: the aqueous polymer dispersion of the present invention and a pigment, wherein the pigment is a rutile type titanium dioxide; and wherein the coating composition is light and heat stable. Preferably, the pigment is silica or alumina modified rutile type titanium dioxide. More preferably, the pigment is silica modified rutile type titanium dioxide.

The amount of the pigment in the coating composition ranges from 10 wt % to 60 wt %, preferably from 15 to 50 wt %, more preferably from 22 to 50 wt %, based on the dry weight of the composition.

The coating composition of the present invention inhibit the microbial production by at least 25%; alternatively, the antibacterial coating composition of the present invention exhibit at least a 1-log reduction (≥90% inhibition) of microbial colony forming units per mL; alternatively the antibacterial coating composition of the present invention exhibit at least a 2-log reduction (≥99% inhibition) of microbial colony forming units per mL; alternatively the antibacterial coating composition of the present invention exhibit at least a 6-log reduction (≥99.9% inhibition) of microbial colony forming units per mL. Such microbes include, but are not limited to, *Aureobasidium pullulans, Bacillus cereus, Bacillus thuringiensis, Chaetomium globosum, Enterobacter aerogines, Escherichia coli, Gliocladtum virens, Klebsiella Pheumoniae, Legionella pneumpophila, Listeria Monocytogenes, Mycobacterium tuberculosis, Porphyromonas gingivalis, Proteus mirabilis, Proteus vulgaris, Pseudomonas aeruginosa, Saccharomyces cerevisiae, Salmonella gallinarum, Salmonella typhimurium, Staphylococcus aureus, Staphylococcus epidermidis, Streptococcus agalactiae, Streptococcus faecalis, Streptococcus mutans, Trycophyton malmsten, Vibrio parahaemolyticus, Stachybotrys, Aspergillus niger, Candida albicans* and *Penicillium funiculosum.*

The coating composition is suitable for various coating systems including, such as acrylic coatings, vinyl acrylic coatings, styrene acrylic coatings, powder coatings, solvent acrylic coatings, alkyd resin coatings, solvent urethane coatings, and epoxy coatings.

The composition is suitable for application onto various substrates including bare or pre-painted substrates such as, but not limited to, cement, ceramic, tile, painting, glass, plastic, wood, metal, woven and non-woven textile, and paper; extremely suitable for consumer products with olfaction requirements, which containing or covered by above mentioned substrates.

In the present specification, the technical features in each preferred technical solution and more preferred technical solution can be combined with each other to form new technical solutions unless indicated otherwise. For briefness, the applicant omits the descriptions for these combinations. However, all the technical solutions obtained by combing these technical features should be deemed as being literally described in the present specification in an explicit manner.

The following examples are presented to illustrate the process and the composition of the invention. These examples are intended to aid those skilled in the art in understanding the present invention. The present invention is, however, in no way limited thereby.

EXAMPLES

The experimental methods in the examples, when not described in detail, is contemplated to follow normal conditions in the art, for example, handbooks of polymer chemistry, or follow conditions suggested by chemical or instrument manufacturer.

I. Raw Materials

The following materials were used in the polymerization:

| Abbreviation | Chemical Nature |
| --- | --- |
| BA | Butyl Acrylate |
| MMA | Methyl Methacrylate |

-continued

| Abbreviation | Chemical Nature |
|---|---|
| (M)AA | (Meth)acrylic Acid |
| AAEM | Acetoacetoxyethyl methacrylate |
| SSS | Sodium p-styrenesulfonate |
| MEA | Mono-ethanolamine |
| t-BHP | tert-butyl hydroperoxide |
| EDTA | Tetrasodium salt of ethylenediaminetetraacetic acid |

The following materials were used in the formulation:

| Materials | Function | Supplier |
|---|---|---|
| Propylene glycol | Solvent | |
| Acrysol AP-10 | Thickener | Dow Chemical Company |
| Orotan 1288 | Dispersant | Dow Chemical Company |
| Triton CF-10 | Wetting agent | Dow Chemical Company |
| Dispelair CF-246 | Defoamer | Blackburn |
| Ti-Pure R-706 | Pigment | Dupont |
| CC-1000 | Extender | |
| Opaque Ultra E | Extender | Dow Chemical Company |
| Teaxanol | Solvent | Eastman |
| Acrysol RM-2020 NPR | Thickener | Dow Chemical Company |
| Acrysol RM-8W | Thickener | Dow Chemical Company |

The following processes were used in the examples:

The Heat Aging Color Change Test

Put the samples into oven and preheated to 50° C., the keep 50° C. heating for 10 days, check the samples color.

The results were ranked on a scale of 0 to 4 as described below.

| Rank | Discoloration |
|---|---|
| 0 | serious |
| 1 | strong |
| 2 | medium |
| 3 | light |
| 4 | No |

* The score reach 3 or higher is acceptable

Antibacterial Efficacy of the Dry Coating Film Test

The antibacterial efficacy test of the dry film follows the Chinese standard GB/T 21866-2008, which is modified from JIS Z 2801. The detail information of the test method is described as following:

Inoculum preparation: transferred test *Escherichia coli* organisms onto tryptic soy agar (TSA) slant and incubated at 37° C. for 18~20 hours, transferred the organisms to another fresh TSA slant and incubated again. Diluted the cultured colony in 1/500 tryptic soy broth (TSB) solution (TSB diluted by 0.85% NaCl solution), and diluted *Staphylococcus aureus* colony in 1/100 TSB solution, to achieve 5.0~10.0×105 cfu/mL, respectively.

Test specimen preparation: coated a plastic test panel with the antibacterial coating composition, dried and cut the panel with dry film into 50 mm×50 mm squares.

Blank control: dry-film panel coated with a coating composition without the metal complexed with a (co)polymer or the oxidant.

Test procedure: placed the test specimen in sterilized petri dish. Added 0.4-0.5 mL inoculum onto blank control and test specimen respectively, covered the inoculum with sterile plastic film and avoided bubble. Incubated the dishes at 37° C. and under relative humidity (RH)>90% for 24 hours. Rinsed the specimen with 20 mL elution solution (0.85% NaCl solution, pH 7.0-7.2), added 1 mL the elution solution containing residue microbes onto a nutrition agar dish, incubated at 37° C. for 24 hours and enumerated the microbe colony by the method in Chinese Standard GB/T 4789.2. Make 2 duplicates for each sample.

Calculation of the antibacterial efficiency according to:

$$\text{Antibacterial efficacy } R(\%)=(B-C)/B\times100$$

wherein B(cfu) refers to average residue microbe content of the blank control after 24 h incubation and C(cfu) refers to average residue microbe content of the test specimen after 24 hours incubation.

Example 1

An aqueous dispersion A was prepared as following process: A mixture of 21.52 g of sodium dodecyl benzene sulfonate (19 wt % solution), and 1072.04 g of deionized water was added to the flask and heated to 85° C. under a nitrogen atmosphere. A monomer emulsion (ME) was prepared by mixing 207.14 g of deionized water, 52.80 g of sodium dodecyl benzene sulfonate (19% solution), 782.72 g BA, 742.71 g MMA, 23.83 g MAA.

With the contents of the flask at 85° C., the following materials were added in order: a solution of 7.77 g of sodium carbonate in 53.82 g of deionized water, a mixture of 69.56 g of monomer emulsion and 27.61 g of deionized water, and a solution of 4.68 g ammonium persulfate in 28.08 g deionized water.

The ME was then added to the flask over a period of less than 1.5 hours while maintaining the contents of the flask at a temperature of 87° C. After 50% ME feed in, stop feeding of ME, add 40.33 g AAEM to ME when stirring, then feeding ME again. After the complete addition of the ME, the ME container was rinsed with 56.16 g of deionized water.

After 20 minutes, add a mixture of 3.74 g of a solution of 0.2 wt % iron sulfate in water, 0.75 g of a solution of 1 wt % tetrasodium salt of ethylenediaminetetraacetic acid in water, and 0.1 g sodium bisulfite, then add a solution of 0.2 g of 70% tBHP in 2.5 g of deionized water, keeping for 30 minutes. When the temperature of the solution lower than 70° C., a solution of 1.15 g of 70% tBHP in 28.08 g of deionized water and a solution of 0.95 g of sodium bisulfite in 28.08 g of deionized water were added over a period of less than 40 minutes and the contents of the flask was allowed to cool to 45° C. Next, a solution of 15.08 g glycine in 140 g of 4% sodium hydroxide and 11.3 g Silver complex (3% active silver ion) were added, the contents of the flask were filtered to remove any coagulum. The resulting aqueous polymer dispersion A had a pH of 8.5 and 48.5 wt % solids.

Example 2

An aqueous dispersion B was prepared as following process: A mixture of 21.52 g of sodium dodecyl benzene sulfonate (19 wt % solution), and 1072.04 g of deionized water was added to the flask and heated to 85° C. under a nitrogen atmosphere. A monomer emulsion (ME) was prepared by mixing 207.14 g of deionized water, 52.80 g of sodium dodecyl benzene sulfonate (19% solution), 798.35 g BA, 595.89 g MMA, 23.83 g MAA, 161.34 AAEM.

With the contents of the flask at 85° C., the following materials were added in order: a solution of 7.77 g of sodium carbonate in 53.82 g of deionized water, a mixture of 69.56 g of monomer emulsion and 27.61 g of deionized water, and a solution of 4.68 g ammonium persulfate in 28.08 g deionized water.

The ME was then added to the flask over a period of less than 1.5 hours while maintaining the contents of the flask at a temperature of 87° C. After the complete addition of the ME, the ME container was rinsed with 56.16 g of deionized water.

After 20 minutes, add a mixture of 3.74 g of a solution of 0.2 wt % iron sulfate in water, 0.75 g of a solution of 1 wt % tetrasodium salt of ethylenediaminetetraacetic acid in water, and 0.1 g sodium bisulfite, then add a solution of 0.2 g of 70% tBHP in 2.5 g of deionized water, keeping for 30 minutes. When the temperature of the solution lower than 70° C., a solution of 1.15 g of 70% tBHP in 28.08 g of deionized water and a solution of 0.95 g of sodium bisulfite in 28.08 g of deionized water were added over a period of less than 40 minutes and the contents of the flask was allowed to cool to 45° C. Next, a solution of 109.8 g glycine in 220 g of 4% sodium hydroxide and 11.6 g Silver complex (3% active silver ion) were added, the contents of the flask were filtered to remove any coagulum. The resulting aqueous polymer dispersion B had a pH of 8.2 and 47.2 wt % solids.

Example 3

An aqueous dispersion C was prepared as following process: A mixture of 21.52 g of sodium dodecyl benzene sulfonate (19 wt % solution), and 1072.04 g of deionized water was added to the flask and heated to 85° C. under a nitrogen atmosphere. A monomer emulsion (ME) was prepared by mixing 207.14 g of deionized water, 52.80 g of sodium dodecyl benzene sulfonate (19% solution), 792.72 g BA, 652.00 g MMA, 23.83 g MAA.

With the contents of the flask at 85° C., the following materials were added in order: a solution of 7.77 g of sodium carbonate in 53.82 g of deionized water, a mixture of 69.56 g of monomer emulsion and 27.61 g of deionized water, and a solution of 4.68 g ammonium persulfate in 28.08 g deionized water.

The ME was then added to the flask over a period of less than 1.5 hours while maintaining the contents of the flask at a temperature of 87° C. After 50% ME feed in, stop feeding of ME, add 1.61 g AAEM to ME when stirring, then feeding ME again. After the complete addition of the ME, the ME container was rinsed with 56.16 g of deionized water.

After 20 minutes, add a mixture of 3.74 g of a solution of 0.2 wt % iron sulfate in water, 0.75 g of a solution of 1 wt % tetrasodium salt of ethylenediaminetetraacetic acid in water, and 0.1 g sodium bisulfite, then add a solution of 0.2 g of 70% tBHP in 2.5 g of deionized water, keeping for 30 minutes. When the temperature of the solution lower than 70° C., a solution of 1.15 g of 70% tBHP in 28.08 g of deionized water and a solution of 0.95 g of sodium bisulfite in 28.08 g of deionized water were added over a period of less than 40 minutes and the contents of the flask was allowed to cool to 45° C. Next, a solution of 2.74 g glycine in 120 g of 4% sodium hydroxide and 11.3 g Silver complex (3% active silver ion) were added, the contents of the flask were filtered to remove any coagulum. The resulting aqueous polymer dispersion C had a pH of 8.4 and 48.5 wt % solids.

Example 4

In a similar procedure to aqueous polymer dispersion A (Example 1), an aqueous polymer dispersion D was prepared using a solution of 17.89 g beta-alanine in 140 g of 4% sodium hydroxide as neutralizer. The resulting aqueous polymer dispersion D had 47.7 wt % solids.

Example 5

In a similar procedure to aqueous polymer dispersion A (Example 1), an aqueous polymer dispersion E was prepared using a solution of 20.71 g 4-aminobutyric acid in 140 g of 4% sodium hydroxide as neutralizer. The resulting aqueous polymer dispersion E had 47.8 wt % solids.

Example 6

In a similar procedure to aqueous polymer dispersion A (Example 1), an aqueous polymer dispersion F was prepared using a solution of 26.34 g 6-aminocaproic acid in 140 g of 4% sodium hydroxide as neutralizer. The resulting aqueous polymer dispersion F had 48.0 wt % solids.

Example 7

In a similar procedure to aqueous polymer dispersion A (Example 1), an aqueous polymer dispersion G was prepared using 0.56 g Silver complex (3% active silver ion). The resulting aqueous polymer dispersion G had 48.4 wt % solids.

Example 8

In a similar procedure to aqueous polymer dispersion A (Example 1), an aqueous polymer dispersion H was prepared using 84.75 g Silver complex (3% active silver ion). The resulting aqueous polymer dispersion H had 48.6 wt % solids.

Comparative Example 9

An aqueous dispersion I was prepared as following process: A mixture of 21.52 g of sodium dodecyl benzene sulfonate (19 wt % solution), and 1141.25 g of deionized water was added to the flask and heated to 85° C. under a nitrogen atmosphere. A monomer emulsion (ME) was prepared by mixing 385.00 g of deionized water, 64.80 g of sodium dodecyl benzene sulfonate (19% solution), 978.75. g BA, 590.60 g MMA, 25.10 g MAA, 83.70 AAEM.

With the contents of the flask at 85° C., the following materials were added in order: a solution of 8.30 g of sodium carbonate in 57.50 g of deionized water, a mixture of 74.30 g of monomer emulsion and 29.50 g of deionized water, and a solution of 5.00 g ammonium persulfate in 30.00 g deionized water.

The ME was then added to the flask over a period of less than 1.5 hours while maintaining the contents of the flask at a temperature of 87° C. After the complete addition of the ME, the ME container was rinsed with 60.00 g of deionized water.

After 20 minutes, add a mixture of 4.05 g of a solution of 0.2 wt % iron sulfate in water, 0.80 g of a solution of 1 wt % tetrasodium salt of ethylenediaminetetraacetic acid in water, and 0.12 g sodium bisulfite, then add a solution of 0.25 g of 70% tBHP in 2.5 g of deionized water, keeping for 30 minutes. When the temperature of the solution lower than 70° C., a solution of 1.15 g of 70% tBHP in 28.08 g of deionized water and a solution of 0.95 g of sodium bisulfite in 28.08 g of deionized water were added over a period of less than 40 minutes and the contents of the flask was allowed to cool to 45° C. Next, a solution of 41.6 g of 50% MEA solution and 11.3 g Silver complex (3% active silver ion) were added, the contents of the flask were filtered to remove any coagulum. The resulting aqueous polymer dispersion I had a pH of 8.9 and 48.5 wt % solids.

The resulting samples were then subjected to heat aging color change evaluation and the results as shown in Table 1.

TABLE 1

Heat Aging Color Change Results

| Sample | Discoloration after heat aged |
|---|---|
| Dispersion A | 3 |
| Dispersion B | 3 |
| Dispersion C | 4 |
| Dispersion D | 4 |
| Dispersion E | 4 |
| Dispersion F | 4 |
| Dispersion G | 4 |
| Dispersion H | 4 |
| Comparative I | 0 |

Example 10

A typical latex paint formulation utilizing the aqueous dispersion of the present invention is following (Table 2, 55PVC):

TABLE 2

Formulation of Paint A and B base on the Aqueous Dispersion A and E

| Ingredients (grams) | Paint A | Paint B |
|---|---|---|
| Water | 157.10 | 157.10 |
| Propylene Glycol | 12.00 | 12.00 |
| Acrysol AP-10 | 1.46 | 1.46 |
| AMP-95 | 0.80 | 0.80 |
| Orotan 1288 | 4.01 | 4.01 |
| Triton CF-10 | 2.00 | 2.00 |
| Dispelair CF-246 | 1.00 | 1.00 |
| Ti-Pure R-706 | 230.14 | 230.14 |
| CC-1000 | 125.09 | 125.09 |
| Dispersion A | 283.36 | |
| Dispersion E | | 283.36 |
| Ropaque Ultra E | 100.06 | 100.06 |
| Texanol | 6.00 | 6.00 |
| Dispelair CF-246 | 1.00 | 1.00 |
| Acrysol RM-2020 NPR | 3.00 | 3.00 |
| Acrysol RM-8W | 6.90 | 6.90 |
| Water | 66.08 | 66.09 |
| Total | 1000.0 | 1000.0 |

Paint A and B then be coated on a plastic test panel for antibacterial efficiency test of dry film according to JIS 2801 (Table 3):

TABLE 3

Antibaceterial Efficinecy Test of paint A and B

| | Staphylococcus aureus** | | | Escherichia coli** | | |
|---|---|---|---|---|---|---|
| Paint No. | 1 | 2 | Antibacterial ratio(R)[%]* | 1 | 2 | Antibacterial ratio(R)[%]* |
| Paint blank | 3.2E+06 | 2.56E+06 | control | 1.92E+07 | 1.34E+07 | control |
| Paint A | <20 | <20 | >99.9% | <20 | <20 | >99.9% |
| Paint B | <20 | <20 | >99.9% | <20 | <20 | >99.9% |

Notes:
*R % = (cfu on blank test piece after 24 h − cfu on treated test piece after 24 h)/cfu on blank test piece
**The inoculum of S. aureus is 12,000,000 cfu/test piece. The inoculum of E. coli is 3,100,000 cfu/test piece.

The invention claimed is:

1. An aqueous polymer dispersion comprising:
   a) a polymer comprising, as polymerized units, from 0.1% to 10% by dry weight percentage based on the dry weight of the polymer dispersion, at least one acetoacetoxy or acetoacetamide group containing monomer;
   b) 0.001% to 0.15% by dry weight based on the dry weight of the polymer dispersion, of at least one metal ion selected from copper, silver, gold, tin, and zinc; and
   c) an amino acid, being present in a mole ratio of amino acid to acetoacetoxy or acetoacetamide group containing monomer of from 0.9:1 to 5:1.

2. The aqueous polymer dispersion according to claim 1 wherein the polymer comprises an acetoacetoxy group containing monomer selected from the group consisting of acetoacetoxyethyl(meth)acrylate, acetoacetoxypropyl (meth)acrylate, acetoacetoxybutyl (meth)acrylate, allyl acetoacetate, 2,3-di(acetoacetoxy)propyl (meth)acrylate, and combinations thereof.

3. The aqueous polymer dispersion according to claim 1 wherein the polymer comprises an acetoacetamide group containing monomer having the formula as follows:

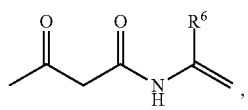

wherein R⁶ is either H or methyl.

4. The aqueous polymer dispersion according to claim 1 wherein the polymer comprises, as polymerized units, at least one nonionic monomer.

5. The aqueous polymer dispersion according to claim 1 wherein the polymer comprises, as polymerized units, at least one ionic monomer.

6. The aqueous polymer dispersion according to claim 1 wherein the metal ion is silver ion.

7. The aqueous polymer dispersion according to claim 1 wherein the amino acid is glycine, 3-aminopropanoic acid, 4-aminobutyric acid, or a mixture thereof.

8. A coating composition comprising the aqueous polymer dispersion according to claim 1.

9. The aqueous polymer dispersion according to claim 1, wherein the amino acid is glycine, 3-aminopropanoic acid, 4-aminobutyric acid, 5-aminovaleric acid, 6-aminocaproic acid, 7-aminohepanoic acid, serine, threonine, tyrosine, beta-alanine, or a combination comprising at least one of the foregoing.

* * * * *